United States Patent [19]
Brewer et al.

[11] Patent Number: 5,991,658
[45] Date of Patent: Nov. 23, 1999

[54] CONTINUAL WAVEFORM SHAPE REFORMING METHOD AND APPARATUS FOR TRANSCHEST RESISTANCE DYNAMICS

[75] Inventors: James E. Brewer, Cottage Grove; Kenneth F. Olson, Edina; Byron L. Gilman, Minnetonka; R. Eric Bosler, St. Paul, all of Minn.

[73] Assignee: SurVivaLink Corporation, Minneapolis, Minn.

[21] Appl. No.: 08/881,662

[22] Filed: Jun. 24, 1997

Related U.S. Application Data

[60] Provisional application No. 60/020,525, Jul. 1, 1996.

[51] Int. Cl.$^6$ ....................................................... A61N 1/39
[52] U.S. Cl. ................................................................. 607/7
[58] Field of Search .......................................... 607/5, 7, 8

[56] References Cited

U.S. PATENT DOCUMENTS

| | | |
|---|---|---|
| 4,768,512 | 9/1988 | Imran . |
| 5,385,575 | 1/1995 | Adams . |
| 5,391,186 | 2/1995 | Kroll et al. . |
| 5,431,686 | 7/1995 | Kroll et al. . |
| 5,468,254 | 11/1995 | Hahn et al. . |
| 5,534,015 | 7/1996 | Kroll et al. ................................. 607/5 |
| 5,540,723 | 7/1996 | Ideker et al. ................................ 607/7 |
| 5,593,427 | 1/1997 | Gilner et al. . |
| 5,601,612 | 2/1997 | Gilner et al. . |
| 5,607,454 | 3/1997 | Cameron et al. . |

FOREIGN PATENT DOCUMENTS

| | | |
|---|---|---|
| WO 95/09673 | 4/1995 | WIPO . |
| WO 95/32020 | 11/1995 | WIPO . |

OTHER PUBLICATIONS

On the Intensity–Time Relations for Stimulation By Electric Currents. II, H.A. Blair, The Journal of General Physiology, Rockefeller Institute for Medical Research, vol. 15, pp. 731–755, 1932.

Optical Truncation of Defibrillation Pulses, Werner Irnich, Pacing and Clinical Electrophysiology, Futura Publishing Co., vol. 18, No. 4, pp. 673–688, Apr. 1995.

Choosing the Optimal Monophasic and Biphasic Waveforms for Ventricular Defibrillation, G.P. Walcott, R. G. Walker, A. W. Cates, W. Krassowska, W. M. Smith, R. E. Ideker, Journal of Cardiovascular Electrophysiology, Futura Publishing Co., vol. 6, No. 9, pp. 737–750, Sep. 1995.

Optimizing Defibrillation Through Improved Waveforms, Michael Block and Günter Breithardt, Pacing and Clinical Electrophysiology, Futura Publishing Co., vol. 18, No. 3, Part II, pp. 526–538, Mar. 1995.

(List continued on next page.)

*Primary Examiner*—William E. Kamm
*Assistant Examiner*—George R. Evanisko
*Attorney, Agent, or Firm*—Patterson & Keough, P.A.

[57] ABSTRACT

The present invention is an external defibrillator which controls and manages the formation of defibrillation waveforms. The waveforms are dynamically adjusted and created to be consistent with a myocardial cell response waveform. Dynamic tilt calculations based on time slices and corresponding functions based on best-fit models are used to generate the waveforms. The waveforms are dynamically adjusted to compensate for changes in resistance due to changes in the voltage during delivery of the waveform. The waveforms include a first and a second phase and are formed with minimal delay therebetween.

14 Claims, 8 Drawing Sheets

OTHER PUBLICATIONS

A Conceptual Basis for Defibrillation Waveforms, Brian G. Cleland, Pacing and Clinical Electrophysiology, Futura Publishing Co., vol. 19, No. 8, pp. 1186–1195, Aug. 1996.

A Minimal Model of the Single Capacitor Biphasic Defibrillation Waveform, Mark W. Kroll, Pacing and Clinical Electrophysiology, Futura Publishing Co., vol. 17, No. 11, Part I, pp. 1782–1792, Nov. 1994.

On The Intensity–Time Relations For Stimulation By Electric Currents. I, H.A. Blair, The Journal of General Physiology, Rockefeller Institute for Medical Research, vol. 15, pp. 709–729, 1932.

Ventricular Defibrillation Using Biphasic Waveforms: The Importance of Phasic Duration, A.S.L. Tang, S. Yabe, J.M. Wharton, M. Doker, W.M. Smith, R.E. Ideker, Journal of the American College of Cardiology, American College of Cardiology, vol. 13, No. 1, pp. 207–214, Jan. 1989.

A Minimal Model of the Monophasic Defibrillation Pulse, Mark W. Kroll, Pacing and Clinical Electrophysiology, Futura Publishing Co., vol. 16, No. 4, Part I, pp. 769–777, Apr. 1993.

Strength–Duration and Probability of Success Curves for Defibrillation With Biphasic Waveforms, S.A. Feeser, A.S.L. Tang, K.M. Kavanagh, D.L. Rollins, W.M. Smith, P.D. Wolf, R.E. Ideker, Circulation, American Heart Association, vol. 82, No. 6, pp. 2128–2141, Dec. 1990.

Improved Defibrillation Thresholds With Large Contoured Epicardial Electrodes and Biphasic Waveforms, E.G. Dixon, A.S.L. Tang, P.D. Wolf, J.T. Meador, M.J. Fine, R.V. Calfee, R.E. Ideker, Circulation, American Heart Association, vol. 76, No. 5, pp. 1176–1184, Nov. 1987.

Truncated Biphasic Pulses for Transthoracic Defibrillation, G.H. Bardy, B.E. Gliner, P.J. Kudenchuk, J.E. Poole, G.L. Dolack, G.K. Jones, J. Anderson, C. Troutman, G. Johnson, Circulation, American Heart Association, vol. 91, No. 6, pp. 1768–1774, Mar. 1995.

Transthoracic Defibrillation of Swine With Monophasic and Biphasic Waveforms, B.E. Gliner, T.E. Lyster, S.M. Dillion, G.H. Bardy, Circulation, American Heart Association, vol. 92, No. 6, pp. 1634–1643, Sep. 1995.

Multicenter Comparison of Truncated Biphasic Shocks and Standard Damped Sine Wave Monophasic Shocks for Transthoracic Ventricular Defibrillation, G.H. Bardy, F.E. Marchlinski, A.D. Sharma, S.J. Worley, R.M. Luceri, R. Yee, B.D. Halperin, C.L. Fellows, T.S. Ahern, D.A. Chilson, D.L. Packer, D.J. Wilber, T.A. Mattioni, R. Reddy, R.A. Kronmal, R. Lazzara, Circulation, American Heart Associate, vol. 94, No. 10, pp. 2507–2514, Nov. 1996.

Low Voltage Shocks Have a Significantly Higher Tilt of the Internal Electric Field Than Do High Voltage Shocks, by James E. Brewer et al., Pacing and Clinical Electrophysiology, vol. 18, No. 1, Jan. 1995.

Mechanisms for Electrical Stimulation of Excitable Tissue, by Roth BJ, Critical Reviews In Biomedical Engineering, 1994, 22 (3–4) p. 253–305 ISSN 0278–940X.

Virtual Electrodes in Cardiac Tissue; A Common Mechanism for Anodal and Cathodal Stimulation; by Wikswo JP Jr.; Lin SF; Abbas RA, Biophysics Journal Dec. 1995, 69(6) p. 32195–210, ISSN 0006–3495.

A Mathematical Model of Make and Break Electrical Stimulation of Cardiac Tissue by a Unipolar Anode or Cathode; by Roth BJ, IEEE Trans Biomed Eng Dec. 1995, 42 (12) p. 1174–84.

The Effect of Externally Applied Electrical Fields on Myocardial Tissue; by Roth BJ and Wilkswo JP, Jr.; Proceedings of the IEEE, Mar. 1996, vol. 84, No. 3, p. 379–391.

On the Intensity–time Relations for Stimulation by Electric Currents; by H.A. Blair, J. Gen. Physiol. 1932; 15: p. 731–755.

The Journal of General Physiology, Rockefeller Institute for Medical Research, vol. 15, pp. 731–755, 1932.

Journal of Cardiovascular Electrophysiology, Futura Publishing Co., vol. 6, No. 9, Sep. 1995.

The Journal of General Physiology, Rockefeller Institute for Medical Research, vol. 15, pp. 708–729, 1932.

Journal of the American College of Cardiology, American College of Cardiology, vol. 13, No. 1, Jan. 1989.

Circulation, American Heart Assocation, vol. 82, No. 6, pp. 2128–2141, Dec. 1990.

Circulation, American Heart Association, vol. 76, No. 5, pp. 1176–1184, Nov. 1987.

Circulation, American Heart Association, vol. 91, No. 6, pp. 1768–1774, Mar. 1995.

Circulation, American Heart Association, vol. 92, No. 6, pp. 1634–1643, Sep. 1995.

Circulation, American Heart Associate, vol. 94, No. 10, pp. 2507–2514, Nov. 1996.

CONTINUAL WAVEFORM SHAPE REFORMING METHOD AND APPARATUS FOR TRANSCHEST RESISTANCE DYNAMICS

REFERENCE TO RELATED APPLICATION

This application is based on U.S. Provisional Application Ser. No. 60/020,525, filed Jul. 1, 1996, and entitled "Continual Waveform Shape Reforming Method and Apparatus for Transchest Resistance Dynamics" the contents of which are herein incorporated by reference and to which priority under 35 U.S.C. §119 is claimed.

FIELD OF THE INVENTION

The present invention generally relates to dynamic and autonomous shape-correction of defibrillation waveforms in external defibrillators. More specifically, the present invention relates to a method and apparatus for continual shape-correction of monophasic or biphasic defibrillation waveforms based on parameters which vary during the delivery of the defibrillation pulse to a cardiac patient.

BACKGROUND OF THE INVENTION

Defibrillation waveforms are typically defined by the energy expended during the delivery of the waveform. The parameters defining the energy are voltage, current and time. Generally, most defibrillator devices use a preset voltage, and assume the impedance of the heart to be about 50Ω. Thus, only the time parameter is a variable. This means that energy delivery is, at best, an approximation based on a range of preset values. The operational specifications for defibrillation waveforms in accordance with the standards of the Association for the Advancement of Medical Instrumentation (AAMI) is indicated to be at a 40% level of accuracy across impedance ranges.

Prior art devices use a single measurement of current at the beginning of a waveform to calculate the resistance. The duration or time is then adjusted to construct the correct energy during the delivery of the defibrillation pulse. One of the limitations of this approach is that it assumes the resistance remains constant throughout the defibrillation pulse delivery. Studies regarding capacitative discharge waveforms demonstrate that electrical impedance increases as voltage decreases, and that this relationship is not simply due to the Ohm's Law. For the stimulation of excitable biological tissues, current decreases at a faster rate than does voltage. This non-linear relationship between impedance and voltage is largely due to the electrode-tissue interface. (*Low Voltage Shocks have a Significantly Higher Tilt of the Internal Electric Field Than Do High Voltage Shocks*, by James E. Brewer, et al, Pacing and Clinical Electrophysiology, Volume 18, No. 1, January 1995).

The assumption that resistance remains constant is particularly erroneous in light of the transchest/transthoracic application shock delivery involving external defibrillators (EDs). The transchest discharge of shock pulses involves chest resistances which include chest wall resistance, lung series resistance, lung parallel resistance, thoracic cage resistance, in addition to resistance of heart and heart cell membrane. Further, external defibrillators are generally used on random patients under emergency situations. Thus patient variability increases the possible variance of resistance across patients. Realizing this, the assumptions and design parameters of the prior art are inadequate to provide a robust and reliable defibrillation pulse delivery suited for implementation in ED devices.

The shape of a defibrillation waveform is a critical element in the successful delivery of a defibrillation waveform. Specifically, prior art defibrillation pulses for monophasic or biphasic waveforms include preset parameters which are used to structure the waveform. For biphasic waveforms, these parameters include an initial voltage of $\phi_1$ and its duration or tilt, and an initial voltage of $\phi_2$ and its duration or tilt. Additionally, the interphase duration between $\phi_1$ and $\phi_2$ is set to account for interphase delay required to switch from one phase to the other.

Prior art waveform generation assumptions and calculations contain several limitations. Specifically, the waveforms are not congruent with the myocardial cell response. The theory of myocardial cell response is based on the observation that $\phi_1$ defibrillates the heart and for biphasic waveforms $\phi_2$ performs a stabilizing action that keeps the heart from refibrillating by canceling out (burping) any residual charges in the myocardial cells. For monophasic waveforms, these parameters include the initial voltage and the pulse duration or tilt. Further, the efficacy and advantages of monophasic and biphasic waveform pulses is significantly enhanced if the phases are shaped to simulate the myocardial cell response waveform. For biphasic waveforms, the congruence in simulation between the waveform and the myocardial cell response requires that the residual charges be removed immediately after the delivery of $\phi_1$. This implies that there should be no interphase delay between the phases. Moreover, the dynamically changing parameters such as the resistance and the myocardial cell response require that the waveform tilt equation and the duration of the phases must take these variables into account.

Accordingly, there is a need to provide a method and device to enable an autonomous and accurate delivery of a monophasic or biphasic defibrillation waveform which is compatible with the dynamic myocardial cell response in a variable resistance environment.

SUMMARY OF THE INVENTION

The present invention provides an autonomous method and device to continually and dynamically reform the shape of a defibrillation waveform consistent with a myocardial cell response profile. Particularly, the invention is focused on continual waveform shape-correction for variable resistances encountered in the transchest delivery of defibrillation pulses to random patients.

The present invention divides the defibrillation waveform into discrete time-slices. The time slices may be fixed or variable increments of time slices. For example, a typical time-slice may be 1 millisecond. The voltage and the current are measured at each time slice and the instantaneous resistance is calculated for each measurement at each time-slice. In this manner the value of the variable resistance is monitored based on the selected time-slice. A highly refined and accurate monitoring of the variability of the resistance can be executed by choosing a smaller time-slice. Therefore, if voltage and current or resistance are monitored throughout the waveform, the actual energy can be adjusted even if the resistance is fluctuating from one time-slice to the next. Thus, the present invention enables a dynamic adjustment of the duration of the phase of a monophasic waveform or each phase of a biphasic waveform relative to the change in resistance. A dynamic waveform tilt equation is generated by an algorithm to operate the defibrillation discharge consistent with the variability of resistance and the myocardial cell response.

Accordingly, it is an object of the present invention to provide a reliable method and device for delivering dynamically shaped continuous exponential defibrillation pulses to a cardiac patient via electrodes. The electrodes are connected to a voltage source and a control circuit of an external defibrillator device wherein an algorithm implemented in the control circuit imposes a stopping rule to create waveforms which comply with the variability of resistance and the myocardial cell response waveform of the patient. Generally, the method includes continuously measuring a discharge voltage and current based on discrete time slices. The time slices include an initial time slice and a series of other discrete time slices. The resistance is calculated relative to the voltage and current measurements at each time slice. Two waveform tilts are then calculated at each time slice. The first waveform tilt, the actual waveform tilt, is the tilt calculated as the difference between the initial pulse voltage and the voltage measured at each time slice. The second waveform tilt, the cell response waveform tilt, is the tilt calculated according to the myocardial cell response model. The delivery of the pulse is continued and a string of calculations yielding these two waveform tilts and voltages are calculated for each of the time slices. The delivery of the pulse is suspended when the actual waveform tilt becomes greater than or equal to the cell response waveform tilt.

It is a further object of the present invention to provide a reliable and adjustable defibrillation pulse energy device for transchest defibrillation shock treatment of a random patient such that a phase independent algorithm, implemented in the device, generates a waveform from a tilt expression. The tilt expression is dynamically set for a monophasic waveform and for each phase of a biphasic waveform and is a function of resistance. The tilt expression is based on resistance measurements at the electrode-tissue boundaries and in compliance with myocardial cell response.

With these and other objects, advantages and features of the invention that may become hereinafter apparent, the nature of the invention may be more clearly understood by reference to the following detailed description of the invention, the appended claims and to the drawings herein.

DETAILED DESCRIPTION OF THE INVENTION

The present invention is described hereinbelow. However, in order to fully set the background and distinguish the principal parts of the present invention, a brief discussion of the associated circuitry for the external defibrillator will be presented first.

Related Circuitry

Figure 1:
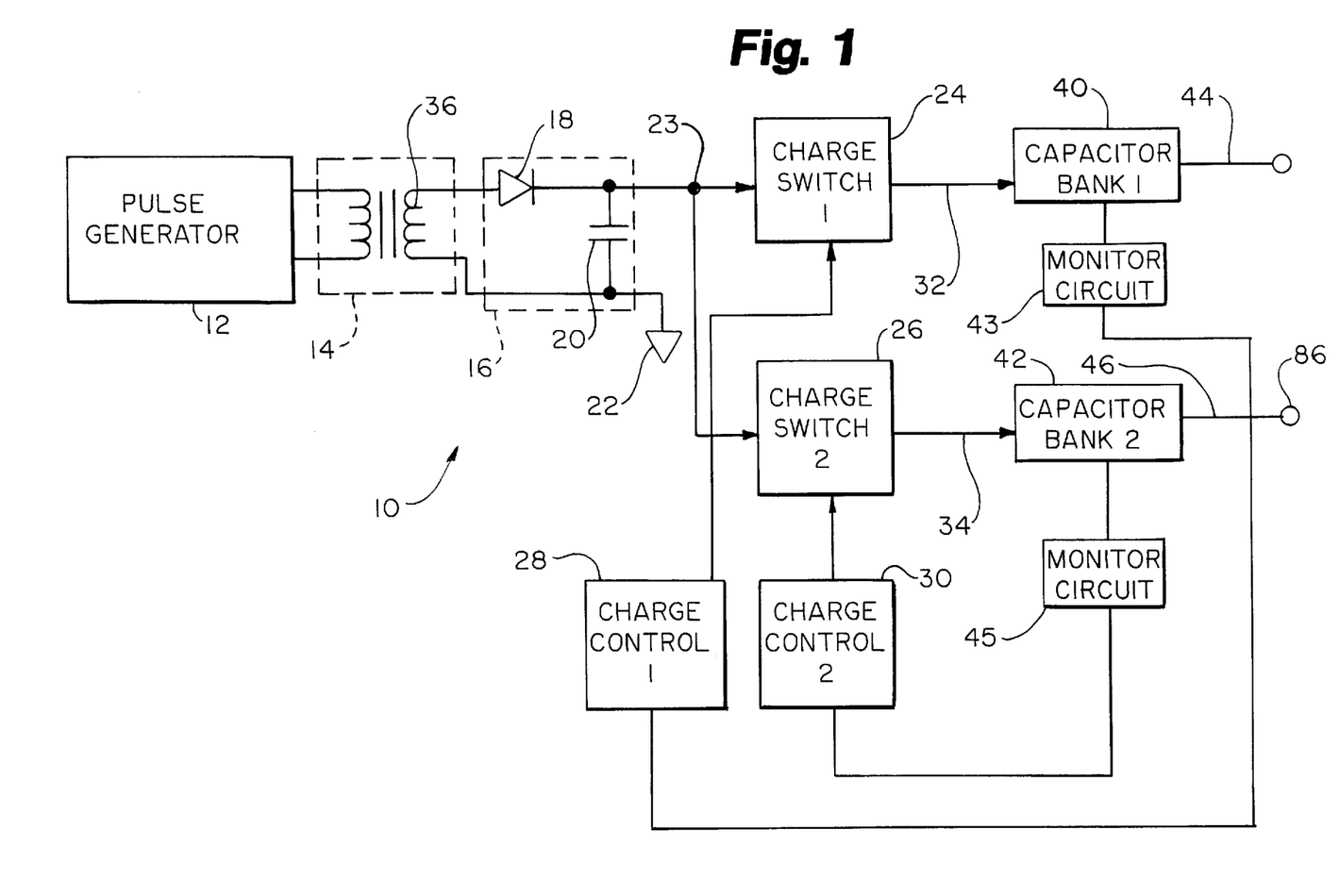
FIG. 1 is a block diagram of a capacitor charge control circuit associated with the present invention.

Referring now to FIG. 1, a charge control circuit 10 may be seen. Circuit 10 includes a pulse generator 12 connected to a pulse transformer 14 which is connected to a passive rectifying and filtering circuit 16. Circuit 16 is preferably made up of a high speed (fast recovery) diode 18, which is preferably a UF4007 type, available from General Instruments, and a capacitor 20 which may be in the range of 3–10 microfarads. Circuit common is indicated by an inverted triangle 22, and an output 23 of the rectifying and filtering circuit 16 is connected to first and second charge switches 24, 26. Charge switches 24, 26 are each preferably formed of one or more solid state switching devices such as a silicon controlled rectifier (SCR), a field effect transistor (FET), or an insulated gate bipolar transistor (IGBT). Such devices may be connected in series (to increase voltage capability) or in parallel (to increase current capability) as is well known in the art. Each of the charge switches 24, 26 is controlled by a separate one of a pair of charge control circuits 28, 30.

The respective outputs 32, 34 of the charge switches 24, 26 are individually connected to one of a pair of capacitor banks 40, 42. Output 32 is connected to a first capacitor bank 40, and output 34 is connected to a second capacitor bank 42. This portion of the circuitry will be described in detail with reference to a pair of capacitor banks but it should be noted that additional capacitor banks may also be included without departing from the spirit or scope of the invention. The output of capacitor bank 40 is connected to an electrode terminal 47 and the output of capacitor bank 42 is connected to an electrode terminal 49.

The circuit is designed to output to electrode terminals 47 and 49 a high voltage defibrillation pulse in the range of approximately 2000–3000 volts in the preferred embodiment. It should be noted however that greater or lesser discharge voltages can also be delivered without departing from the spirit or scope of the invention. In order to generate and deliver the voltage levels desired for defibrillation, a two step process is required. The first step is that of charging the capacitors. The second step is that of discharging the capacitors. To charge low cost, reliable capacitors rapidly to the desired voltage levels, the present invention utilizes charge control circuits 28, 30 and charge switch circuits 24, 26 to charge the capacitors in parallel. When connected in parallel, the total capacitance of a particular capacitance bank is the sum of all the capacitors connected in parallel, while the voltage across each of the individual capacitors is equal. To discharge the capacitors to electrode terminals 47, 49, charge control circuits 28, 30 and charge switch circuits 24, 26 configure the capacitors of a capacitor bank in series. This reduces the total capacitance to a fractional value of the individual capacitors and increase the voltage to the sum of the voltages across each individual capacitor.

The capacitor banks are preferably of differing capacitive values or differing voltage capacities. For example, in one embodiment, capacitor bank 40 has a total capacitance of 7200 microfarads while capacitor bank 42 has a total capacitance of 440 microfarads when connected in parallel for charging. Therefore, capacitor bank 42 will charge much more rapidly than will capacitor bank 40. During discharge, capacitor bank 40 has a total capacitance of 200 microfarads while capacitor bank 42 has a total capacitance of 110 microfarads while connected in series. It should be noted that many other capacitor banks could be utilized having many different capacitance values, or all having the same capacitance value without departing from the spirit or scope of the invention.

The operation of the charge control circuit 10 is as follows. Pulse generator 12 supplies a series, or train, of preferably square wave pulses, typically at a 50% duty cycle and having an amplitude of approximately 400 volts, at a frequency preferably between 5 KHz and 500 KHz. These pulses have a very rapid rise time. Since the fast rise times and high frequencies of the pulses cause avalanching of most common solid state devices of reasonable cost, the pulses are first passed through passive filter circuit 16. Diode 18 is a fast recovery diode that provides for charging of capacitor 20 and prevents discharge of the capacitor 20 through secondary 36 of pulse transformer 14. Capacitor 20 is preferably selected to be able to absorb and store the energy from at least one charge pulse from pulse generator 12.

As stated above, use of a pulse train with a very rapid rise time on individual pulses is desired, but would lead to avalanche breakdown of standard switches if coupled directly thereto. This would cause the switches to lose control of charging, and may lock the switches on, causing the capacitors to be continually charged until they are destroyed. This consequent loss of charging control is unacceptable. Use of rectifying and filtering circuit 16 avoids such avalanche triggering of solid state switches 24, 26 by keeping high dV/dt values from reaching switches 24, 26, allowing ordinary solid state devices to be used for switches 24, 26.

Circuit 10 also includes voltage monitoring circuits 43, 45 for monitoring the voltage on capacitor banks 40 and 42, respectively. Monitor circuits 43 and 45 are connected to the respective capacitor banks and charge control circuit. Monitoring circuits 43 and 45 are illustrated schematically as block diagrams because there are many different embodiments of monitoring circuits that may be used without departing from the spirit or scope of the invention, such as analog circuitry, digital circuitry and solid state components, for example.

Figure 2:
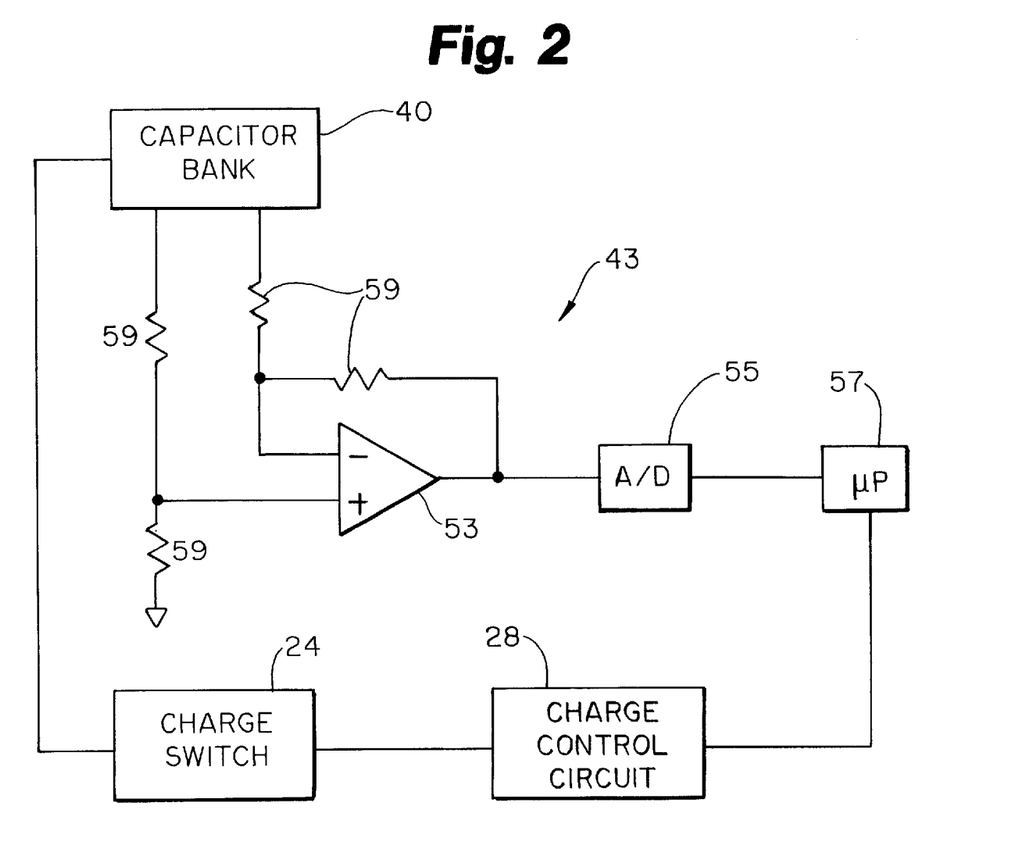
FIG. 2 illustrates one embodiment of the monitoring circuit illustrated in FIG. 1.

FIG. 2 illustrates one preferred embodiment of monitoring circuit 43. It should be noted that monitoring circuit 45 is the same as monitoring circuit 43. As can be seen, an operational amplifier 53 is provided as is an analog to digital converter 55 and a microprocessor 57. Amplifier 60 is connected to capacitor bank 40 via a plurality of resistors 59.

In operation, monitoring circuit 43 has a database of preset values stored in microprocessor 57. When capacitor bank 40 reaches the preset value selected in processor 57, charge control circuit 28 is instructed to halt the charging of capacitor bank 40. In an alternative embodiment, microprocessor 57 has the capability of computing an appropriate predetermined value for charging the respective capacitor bank.

When in the charging mode, one or a plurality of capacitor banks may be charged simultaneously. In the embodiment illustrated in FIG. 1 having first and second capacitor banks 40 and 42, if both capacitor banks 40 and 42 are being simultaneously charged, when capacitor bank 42 is fully charged, charge switch 26 is opened as a result of a command from monitoring circuit 45 and all of the charge available at capacitor 20 is then applied to capacitor bank 40 instead of splitting it between the two capacitor banks. When capacitor bank 40 is completely charged, charge switch 24 is opened as a result of a command from monitoring circuit 43. Capacitor banks 40 and 42 are now fully charged and the individual capacitors that make up a capacitor bank are ready to be switched into series for discharge.

Figure 3:
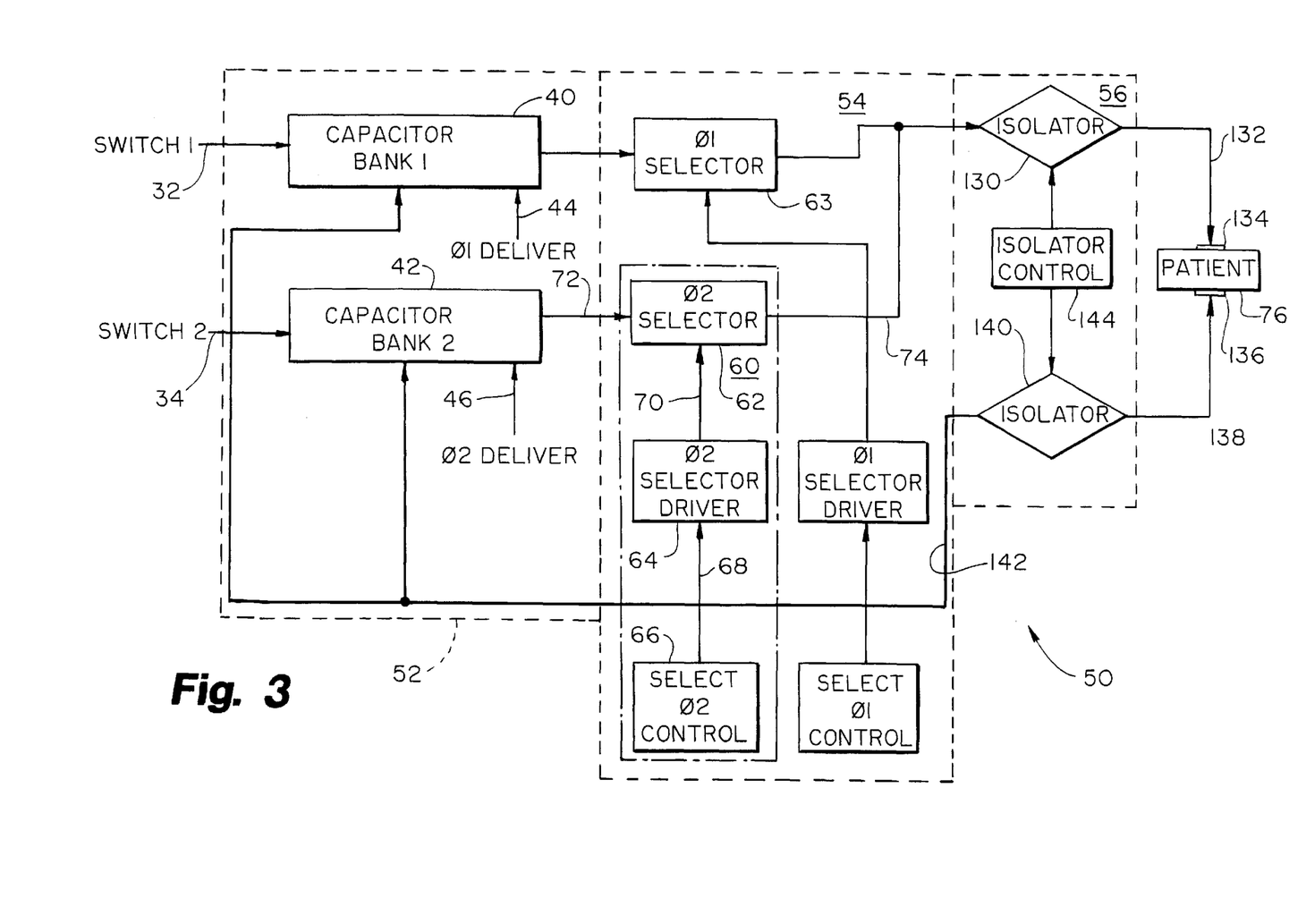
FIG. 3 is a block diagram of a capacitor bank selector an isolation subsystem useful in the practice of the present invention.

Referring now to FIG. 3, an output circuit 50 suitable for providing biphasic defibrillation pulses may be seen. Output circuit 50 includes a capacitor bank circuit 52, a selector circuit 54, and an isolator circuit 56. The capacitor bank circuit includes first and second capacitor banks 40, 42, each of which have respective phase delivery command lines 44, 46. In the preferred embodiment of the present invention, capacitor bank 40 is configured to discharge a positive first phase of the biphasic output pulse while capacitor bank 42 is configured to discharge a negative second phase. It should be noted that additional capacitor banks can be added without departing from the spirit or scope of the present invention. Selector circuit 54 has a pair of preferably identical selector subsystems. One subsystem 60 is indicated by a chain line. Subsystem 60 includes a solid state phase selector switch 62 connected to a phase selector driver 64 which in turn is connected to a select phase control 66. It is to be understood that select phase control 66 provides a signal on line 68 to activate and deactivate phase selector driver 64.

When phase selector driver 64 is activated, it drives phase selector switch 62 to a state of conduction (ON) between lines 72 and 74, connecting capacitor bank 42 to isolator circuit 56 and ultimately to a patient when isolator circuit is itself in a conducting state as will be described infra. When select phase control 66 deactivates phase select driver 64, phase selector switch 62 is rendered nonconductive (OFF) between lines 72 and 74, thus stopping any remainder of the portion of a biphasic defibrillation pulse from being delivered from the capacitor bank 42 to a patient 76. It is to be understood that the phase 1 selector subsystem (connected to capacitor bank 40) is formed of the same elements and operates identically to subsystem 60 in the embodiment shown in FIG. 4. To provide a monophasic defibrillation pulse, only the phase 1 selector subsystem is activated, since capacitor bank 40 is connected to provide a positive polarity output and capacitor bank 42 is connected to provide a negative polarity output.

When providing biphasic defibrillation pulse, it has been found preferable to proceed according to the following sequence:

1. Turn phase 1 selector switch ON, providing a first, positive polarity, exponentially decaying portion of the pulse.

2. Turn phase 1 selector switch OFF, truncating the first portion of the pulse at a desired point.
3. After a time delay, turn phase 2 selector switch ON, providing a second, negative polarity, exponentially decaying portion of the pulse.
4. Turn phase 2 selector switch OFF, truncating the second portion of the pulse at a desired point.

One important aspect of the present invention is the reduction of the transition time between phase 1 and phase 2. In known systems utilizing SCRs as switching mechanisms, any charge in the capacitors must be reduced below the level of the holding current for the SCR before a phase shift can occur. This can take up to 10 seconds due to the large amount of charge typically remaining on the capacitors. This is so even though photoflash capacitors are typically utilized due to their rapid discharge. In these known systems, SCR dump circuits are also required which are complicated circuits which require many components for each capacitor in the capacitor bank and which force the device to throw away all current stored in the bank.

In the present invention, the SCR's have been replaced by IGBT's and photoflash capacitors are no longer needed, allowing more economical, mass-produced products to be used. The delay of switching between phase 1 and phase 2 depends only on the length of time to shut off phase 1 long enough to allow phase 2 to be energized. This time frame is on the order of microseconds. The discharge of current from either capacitor bank 40, 42 may be halted at any time and is able to do so even when voltage levels are in excess of 2000–3000 volts. The discharge of an extremely high voltage phase of opposite polarity is begun within 2–3 microseconds following the truncation of the first phase.

Figure 4:
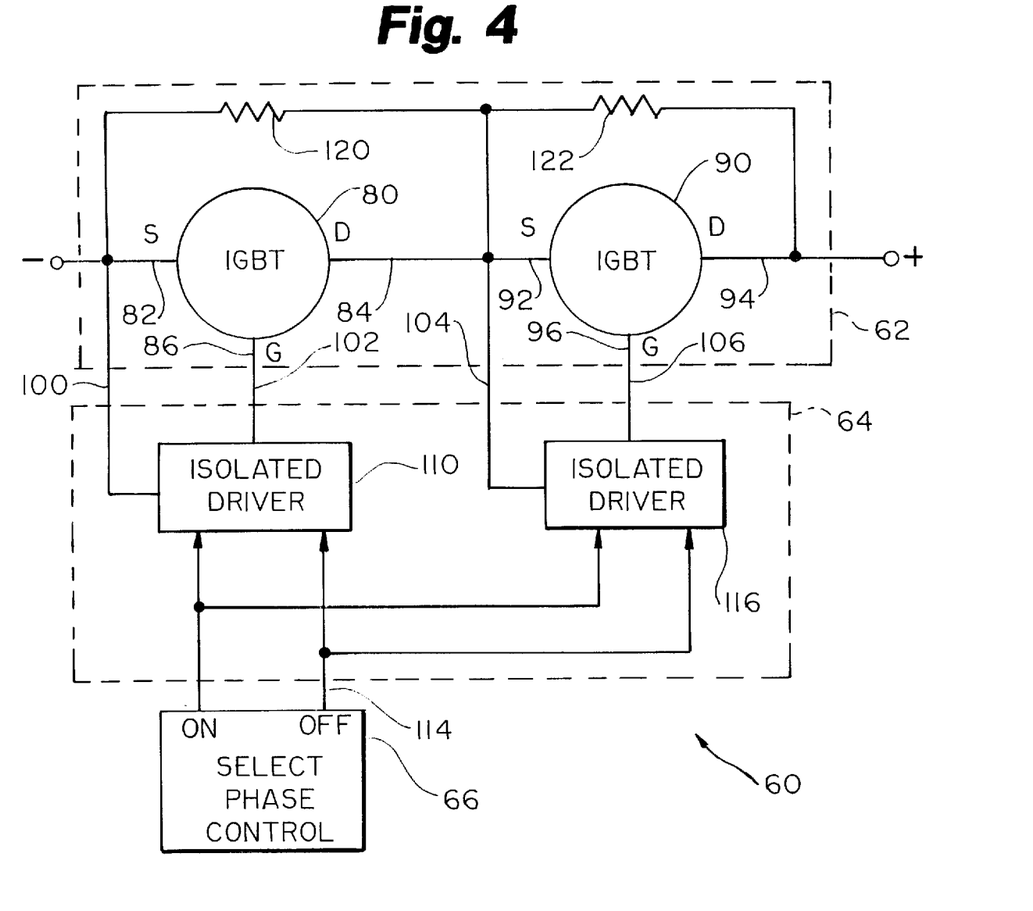
FIG. 4 is a more detailed block diagram of an individual selector, driver and control useful in the practice of the present invention.

Referring now to FIG. 4, details of the phase selector switch 62 may be seen. The preferred embodiment will be described with reference to a pair of IGBT's, but it should be noted that more may be used as will be described below. To withstand the high voltages and high currents encountered in providing defibrillation pulses (whether monophasic or biphasic) two IGBT's are connected in series. As stated in the background section, extremely high voltage and current levels are present in external defibrillators. Voltage levels on the order of 2000–3000 volts and currents in excess of 100 amps are common. A first IGBT 80 has a power input 82 and a power output 84 and a signal input or gate 86. Similarly, a second IGBT 90 also has a power input 92, a power output 94, and a signal input, or gate, 96. Referring now also to FIG. 4, power input 82 is connected to lead 72 carrying the output of capacitor bank 42. Power output 84 is connected to power input 92 and power output 94 is connected to lead 74. The connection 70 between phase selector driver 64 and phase selector switch 62 is actually made up of four connections 100, 102, 104, 106. Connections 100 and 102 couple an isolated driver 110 to IGBT 80. Similarly connection 68 between the select phase control 66 and the phase selector driver 64 actually includes two leads 112, 114. As is shown, driver 116 for IGBT 90 (and associated connections) is identical to that described in connection with driver 110. Each of IGBT's 80, 90 is preferably rated to deliver a 360 Joule pulse into a 25 ohm load [at pulse repetition rate of 1 per 5 seconds], and is also preferably rated to withstand 1200 volts in the OFF condition. One such IGBT is type is IXGH25N120A available from IXYS. To prevent unbalanced voltage between IGBT's 80, 90 in the OFF condition, resistors 120, 122 are connected in series with each other and in parallel as a voltage divider across the series connection of IGBT's 80, 90. The resistance of each resistor 120, 122 is preferably 3 mega ohms.

By adding additional IGBT's or by using IGBT's having higher current and voltage limits, the circuit can output each phase successfully at any current or voltage level. Specifically, the present invention allows the switching from phase 1 to phase 2 at voltage levels greater than 1000 volts. For example, by putting four 1200 volt IGBT's in series for each phase, the circuit can withstand (or hold off) 4800 volts per phase or a total of 9600 volts.

The operation of selector subsystem 60 is as follows. When it is desired to turn phase selector switch 62 ON, a low level signal is generated by select phase control 66, providing a logic ON signal on lead 112 and removing a logic OFF signal on lead 114. Drivers 110 and 116 may be any type of voltage isolating driver circuits sufficient to meet the speed and voltage requirements of the defibrillator system. Presently, magnetically isolated conventional driver circuits are preferred. When it is time to turn off phase 1, IGBT's 80 and 90 are closed thus halting the output to the patient without dumping the charge through an auxiliary SCR dumping circuit. The same is done for phase 2. During the time that the current flows through the IGBT's, peak currents are all within the safe operating areas.

Because dumping the charge in capacitor banks 40 and 42 is not needed to change phases, any dumping circuitry desired can be constructed from lower power components because time is not critical. This greatly reduces the size and cost of the components required.

Present Invention

The disclosure hereinabove generally relates to the circuitry associated with the present invention. However, the elements of the present invention are adaptable to an equivalent or similar circuits and are therefore not limited to the circuit disclosed in supra.

The present invention delivers both monophasic and biphasic waveforms as external defibrillation shock pulses. The monophasic waveform and phase one ($\phi_1$) of the biphasic waveform of the present invention define the voltage and capacitance parameter values that permit the delivery of an AAMI approved 360 J monophasic waveform. The third parameter that defines a monophasic waveform is duration ($d_1$). For the present invention's monophasic waveform, the duration of the monophasic pulse is defined as that length of pulse delivery time that optimizes the delivery of current across the myocardium. Two theories provide rationales for choosing an optimal $d_1$. These theories are the Kroll-Irnich theory of effective current and the Blair-Walcott theory of maximal cell response. The present invention's monophasic waveform has a duration based on each of these two theories. The duration also serves as the $\phi_1$ duration of the biphasic waveform.

For the present invention's biphasic waveform, the duration ($d_2$) of phase two ($\phi_2$) is defined as that length of pulse delivery time that optimizes the charge burping of current remaining on those cells not captured by $\phi_1$. The charge burping theory of Kroll-Walcott provides the rationale and method for designing $\phi_2$. The biphasic waveform has a duration $d_2$ based on the charge burping theory. The theories and their associated models were augmented for transthoracic defibrillation. The design principles determine the optimal waveform characteristics of external truncated exponential waveforms based on these effective current and myocardial cell response models. These theories and their associate models are extended by incorporating the Lerman-Deale resistive network model of a thorax. The extended model is called the transchest defibrillation model and is illustrated in FIG. 5.

Figure 5:
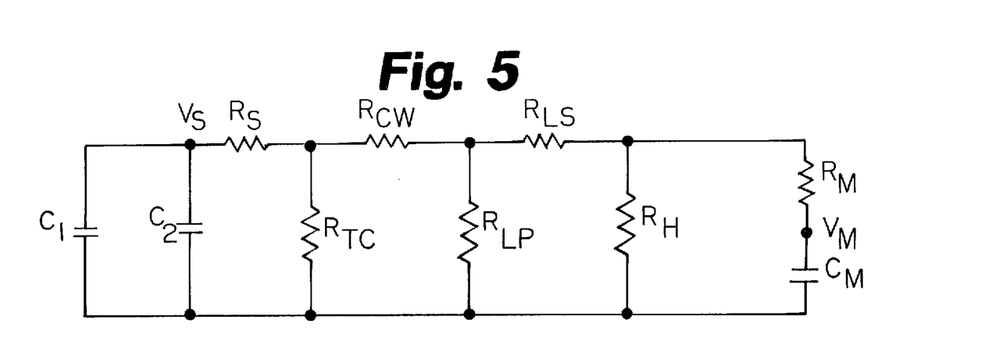
FIG. 5 is a cell response model useful in setting the theoretical background for the transchest waveform design of the present invention.

Referring now to FIG. 5, the transchest augmentation of the myocardial cell response model may be seen. The resistance variables include $R_S$ which is the resistance of the defibrillator, the electrode-electrolyte interface, $R_{TC}$ which represents the resistance of the thoracic cage, $R_{CW}$ representing the resistance of the chest wall, $R_{LP}$ the resistance of the lungs in parallel, $R_H$ the resistance of the pericardium and myocardium and $R_M$ the resistance of the myocardial cell membrane. $C_1$ represents the capacitor in the defibrillator used to deliver $\phi_1$ and $C_2$ the capacitor used to deliver $\phi_2$. $C_M$ represents the cell membrane capacitance and VS represents the forcing function derived from switching $C_1$ or $C_2$ into the circuit model at the time $\phi_1$ or $\phi_2$ is delivered to the heart. $V_M$ represents the transmembrane potential as seen during the delivery of a shock pulse ($V_S$). A defibrillation waveform is designed by determining a value for its characterizing parameter that produces predetermined responses from a myocardial cell as defined by changes in the cell's transmembrane potential over time. The predetermined responses produce either cell depolarization or repolarization prolongation. The governing design procedure which may be derived from the model includes finding $V_S$, as a function of time, in order to produce the desired VM response.

Each theory is based on predetermined values for resistance and other parameters. Additional parameters are chronaxie and the time constant for a myocardial cell membrane. Effective current theory for the design of $\phi_1$ assumes values for resistance and chronaxie. In addition to these two parameters, maximal cell response theory also assumes a value for the cell time constant.

The values for chronaxie and cell time constant are determined experimentally. Studies have estimated the chronaxie for humans in the range of 4 to 6 ms. Using the theory of cell response, a value for the cell time constant can be estimated placing the cell time constant in the range of approximately 4 to 8 ms. The present invention waveforms employ a human chronaxie of 5 ms. A value of 4 was employed for the cell time constant. It should be noted that these ranges are given only as examples and are not limitations. Also, neither the waveforms nor the delivery algorithm are substantially altered by changing these values within the preferred ranges. The present invention is capable of recalculating the tilt relations in the microprocessor whenever the programmable parameters are changed. Set forth below are a number of tables illustrating numerous examples of parameters for the different models. It should be again noted that these tables are set forth as illustrations only.

The preferred monophasic waveform and $\phi_1$ of the biphasic waveform have a capacitance of 200 $\mu$F. The characterizing parameter values for the monophasic waveform and $\phi_1$ of the biphasic waveform are illustrated in Table IA and IB.

TABLE IA

Parameters for Blair-Walcott $\phi_1$.

| Resistance ($\Omega$) | $\phi_1$ Time Constant (ms) | $\phi_1$ Duration ($d_1$, ms) | Trailing-Edge Voltage Ratio | $\phi_1$ Tilt (%) | Relative Cell Response |
|---|---|---|---|---|---|
| 40 | 8 | 6.20 | 0.461 | 54% | 0.243 |
| 60 | 12 | 7.40 | 0.540 | 46% | 0.286 |
| 80 | 16 | 8.35 | 0.593 | 41% | 0.316 |
| 100 | 20 | 9.10 | 0.634 | 37% | 0.339 |

TABLE IA-continued

Parameters for Blair-Walcott $\phi_1$.

| Resistance ($\Omega$) | $\phi_1$ Time Constant (ms) | $\phi_1$ Duration ($d_1$, ms) | Trailing-Edge Voltage Ratio | $\phi_1$ Tilt (%) | Relative Cell Response |
|---|---|---|---|---|---|
| 120 | 24 | 9.75 | 0.666 | 33% | 0.356 |
| 140 | 28 | 10.30 | 0.692 | 31% | 0.370 |

TABLE IB

Parameters for Kroll-Irnich $\phi_1$.

| Resistance ($\Omega$) | $\phi_1$ Time Constant (ms) | $\phi_1$ Duration ($d_1$ ms) | Trailing Edge Voltage Ratio | $\phi_1$ Tilt (%) | Relative Cell Response |
|---|---|---|---|---|---|
| 40 | 8 | 7.60 | 0.387 | 61% | 0.237 |
| 60 | 12 | 9.55 | 0.451 | 55% | 0.277 |
| 80 | 16 | 11.25 | 0.495 | 51% | 0.302 |
| 100 | 20 | 12.70 | 0.530 | 47% | 0.321 |
| 120 | 24 | 14.05 | 0.557 | 44% | 0.335 |
| 140 | 28 | 15.25 | 0.580 | 42% | 0.347 |

TABLE IIA

The parameter values for Blair-Walcott $\phi_2$ with 110 $\mu$F capacitance and 1$^{st}$-order charge burping.

| Resistance ($\Omega$) | $\phi_2$ Time Constant (ms) | $\phi_2$ Duration ($d_2$) | Trailing Edge Voltage Ratio | $\phi_2$ Tilt (%) |
|---|---|---|---|---|
| 40 | 4.4 | 3.65 | 0.436 | 56% |
| 60 | 6.6 | 3.70 | 0.571 | 43% |
| 80 | 8.8 | 3.75 | 0.653 | 35% |
| 100 | 11.0 | 3.80 | 0.708 | 29% |
| 120 | 13.2 | 3.85 | 0.747 | 25% |
| 140 | 15.4 | 3.90 | 0.776 | 22% |

TABLE IIB

Parameters for Blair-Walcott $\phi_2$ with 30 $\mu$F capacitance and 2$^{nd}$-order charge burping.

| Resistance ($\Omega$) | $\phi_2$ Time Constant (ms) | $\phi_2$ Duration ($d_2$) | Trailing-Edge Voltage Ratio | $\phi_2$ Tilt (%) |
|---|---|---|---|---|
| 40 | 1.2 | 11.95 | 0.000 | 100% |
| 60 | 1.8 | 9.95 | 0.004 | 100% |
| 80 | 2.4 | 7.65 | 0.041 | 96% |
| 100 | 3.0 | 6.35 | 0.120 | 88% |
| 120 | 3.6 | 5.75 | 0.203 | 80% |
| 140 | 4.2 | 5.40 | 0.277 | 72% |

TABLE IIC

The parameter values for Kroll-Irnich $\phi_2$ with 110 $\mu$F capacitance and 1$^{st}$-order charge burping.

| Resistance ($\Omega$) | $\phi_2$ Time Constant (ms) | $\phi_2$ Duration ($d_2$) | Trailing-Edge Voltage Ratio | $\phi_2$ Tilt (%) |
|---|---|---|---|---|
| 40 | 4.4 | 3.55 | 0.446 | 55% |
| 60 | 6.6 | 3.60 | 0.580 | 42% |
| 80 | 8.8 | 3.65 | 0.661 | 34% |
| 100 | 11.0 | 3.65 | 0.718 | 28% |

TABLE IIC-continued

The parameter values for Kroll-Irnich $\phi_2$ with 110 $\mu$F capacitance and 1$^{st}$-order charge burping.

| Resistance ($\Omega$) | $\phi_2$ Time Constant (ms) | $\phi_2$ Duration ($d_2$) | Trailing-Edge Voltage Ratio | $\phi_2$ Tilt (%) |
|---|---|---|---|---|
| 120 | 13.2 | 3.70 | 0.756 | 24% |
| 140 | 15.4 | 3.75 | 0.784 | 22% |

TABLE IID

The parameter values for Kroll-Irnich $\phi_2$ with 30 $\mu$F capacitance and 2$^{nd}$-order charge burping.

| Resistance ($\Omega$) | $\phi_2$ Time Constant (ms) | $\phi_2$ Duration ($d_2$) | Trailing-Edge Voltage Ratio | $\phi_2$ Tilt (%) |
|---|---|---|---|---|
| 40  | 1.2 | 11.85 | 0.000 | 100% |
| 60  | 1.8 | 9.70  | 0.005 | 100% |
| 80  | 2.4 | 7.25  | 0.049 | 95%  |
| 100 | 3.0 | 6.00  | 0.135 | 87%  |
| 120 | 3.6 | 5.40  | 0.223 | 78%  |
| 140 | 4.2 | 5.10  | 0.297 | 70%  |

FIGS. 8A, 8B, 8C and 8D illustrate the preferred biphasic waveforms, based on a total system resistance of 80 $\Omega$ (with transchest resistance $\geq 79 \Omega$). As can be seen, the waveform design theories are not sensitive to absolute voltage values for the leading edges of $\phi_1$ and $\phi_2$.

Figure 6:
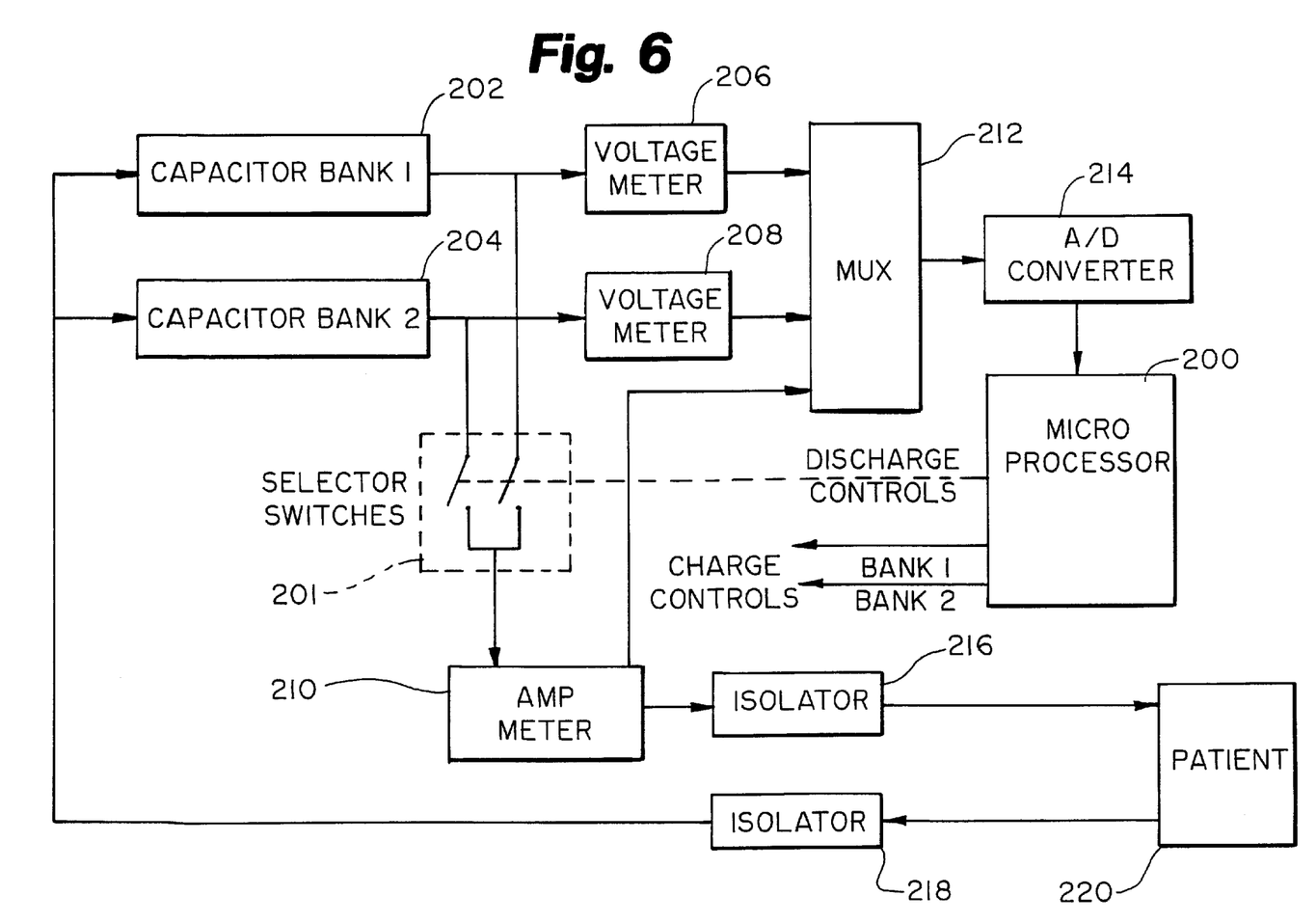
FIG. 6 is a block diagram of the hardware associated with the pulse delivery algorithm of the present invention.

Referring now to FIG. 6, an embodiment of the pulse delivery algorithm hardware and its integration with the external defibrillator circuit is shown. Microprocessor 200 is a programmable unit that controls the defibrillator charge and discharge controls via selector switches 201. Capacitor banks 202 and 204 are discharged to produce the biphasic shock pulses as required. The voltage of the shock is measured by voltmeters 206 and 208 and the amperage is registered by amp meter 210. Multiplexor 212 accepts the analog electrical quantities, voltage from voltmeters 206 and/or 208 and current from amp meter 210, and multiplexes them into a sequence. The multiplexed sequence is transmitted into A/D converter 214 as input. Subsequently, the sequence is digitized and introduced into microprocessor 200. Based on the digitized measurements of voltage and current and an implementation of the stopping rule, microprocessor 200 performs the necessary calculations and starts, continues or stops the discharge of a shock pulse. Isolators 216 and 218 isolate current and voltage sources from patient 220, respectively.

Figure 7:
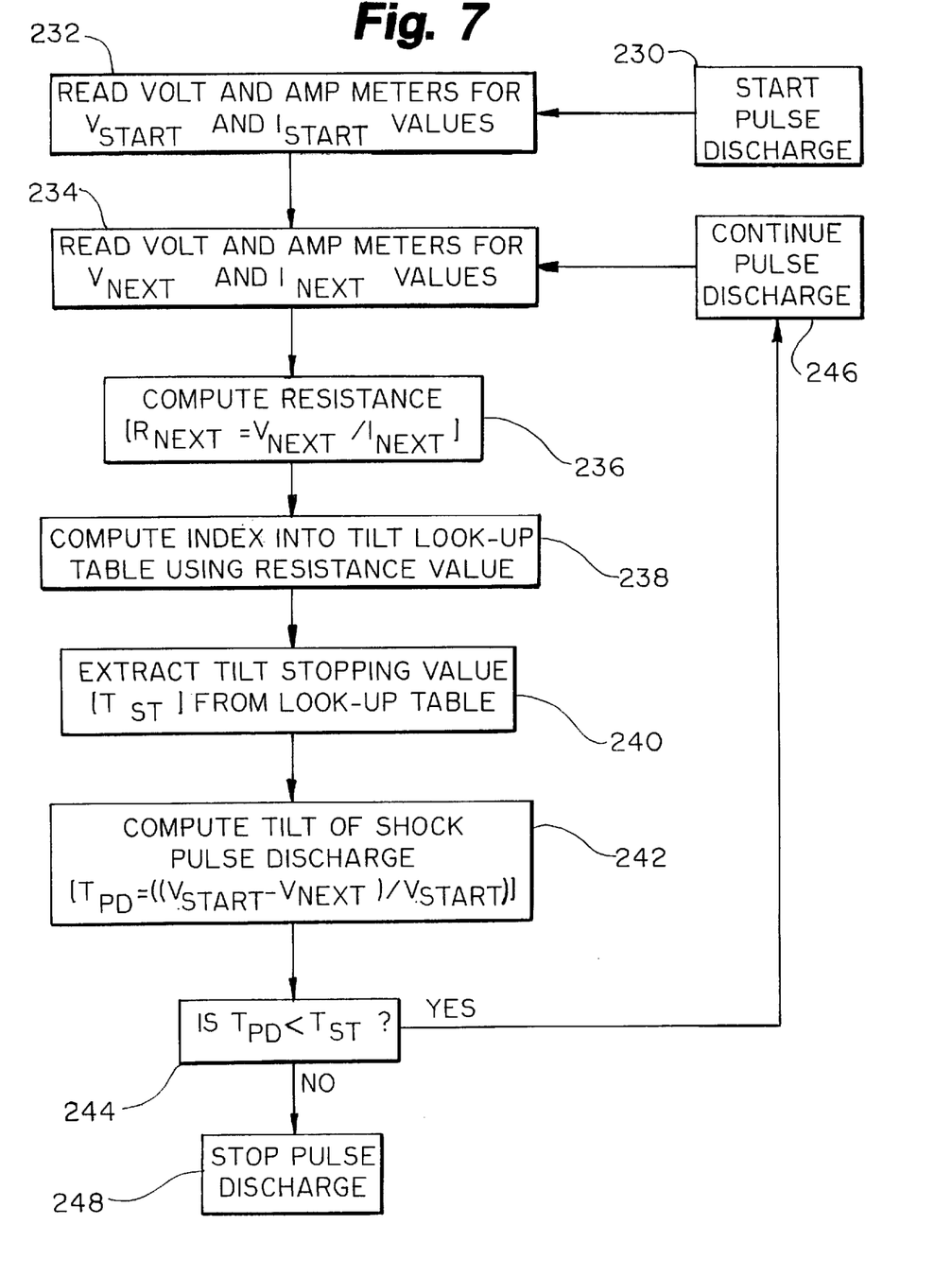
FIG. 7 is a flow chart of the delivery algorithm logic.

FIG. 7 shows a flow chart of the logic of the waveform delivery. The logic is initiated under block 230 when a pulse is discharged from the external defibrillator. The initial voltage and current values are read under block 232. The logic proceeds to block 234 where the next voltage and current values are read. Resistance values are computed under block 236 for the parameters read under block 234. These computed resistance values are used to compute an index into a tilt look-up table under block 238. Thereafter the algorithm proceeds to extract a next tilt stopping value from the look-up table under block 240. The next tilt stopping value is determined at each time slice. The tilt stopping value is one of the significant parameters of the present invention. The algorithm proceeds to calculate a tilt value under block 242 between the initial discharge voltage and the voltage measured based on the time slice. Under decision block 244, the values of the tilts obtained under block 240 and 242 are compared. If the value of the computed tilt under block 242 is less than the tilt stopping value of block 240, the logic proceeds to block 246 where the pulse discharge is continued. In the alternate, if the value of the computed tilt is equal to or greater than the tilt stopping value of block 240, the pulse discharge is terminated.

Accordingly, the algorithm of the present invention enables a continuous measurement of voltage and current during the waveform delivery. The transthoracic resistance is calculated as a function of the voltage and current each time slice these parameters are measured. Thus, the algorithm continually adjusts the duration of the pulse discharge. The algorithm properly adjusts the amount of time needed to discharge the defibrillator capacitors 202 and 204 to compensate for changes in resistance due to the changes in voltage during delivery.

Recent medical research in defibrillation has demonstrated that resistance is a function of voltage (JACC 1989; 13: 207–214) and that this relationship is hyperbolic (PACE 1995; 18 [PtII]: 214–220). Tang (JACC) reported an increase in mean resistance from the first phase of a biphasic waveform to the second using an animal model. He suggested that the resistance changes were primarily at the electrode-tissue interface and his hypothesis was confirmed by Brewer (PACE). Brewer (PACE) went further to determine that the myocardial tissue itself acts as a linear conductor but that a hyperbolic relationship between voltage and resistance does exist at the electrode-tissue interface. Realizing this, the delivery algorithm of the present invention measures resistance as a function of voltage to correct for changes in resistance at the electrode-tissue boundaries. The capability of continually adjusting the discharge duration not only provides a defibrillation shock pulse that automatically compensates for patient to patient differences, but additionally automatically compensates for the effects on the duration of a pulse discharge from voltage-dependent changes in resistance. The delivery algorithm thereby achieves the appropriate duration of a shock pulse in accordance with the implemented calculations for waveform design.

Figure 8A:
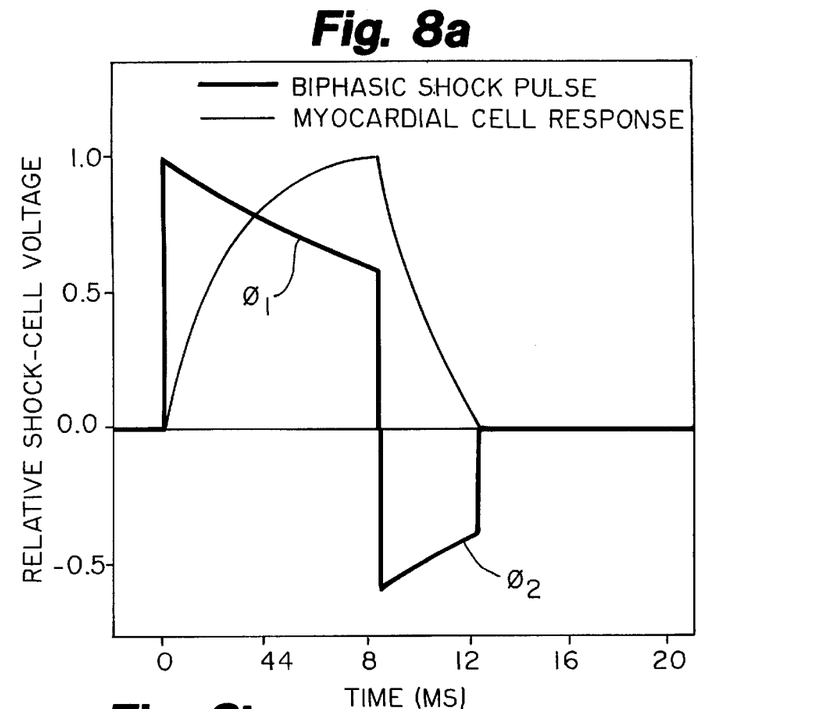
FIG. 8A is a biphasic shock pulse and the associated myocardial cell response generated in accordance with the present invention using Blair-Walcott theory of maximal cell response for the first phase and $1^{st}$ order charge burping for the second phase.
Figure 8B:
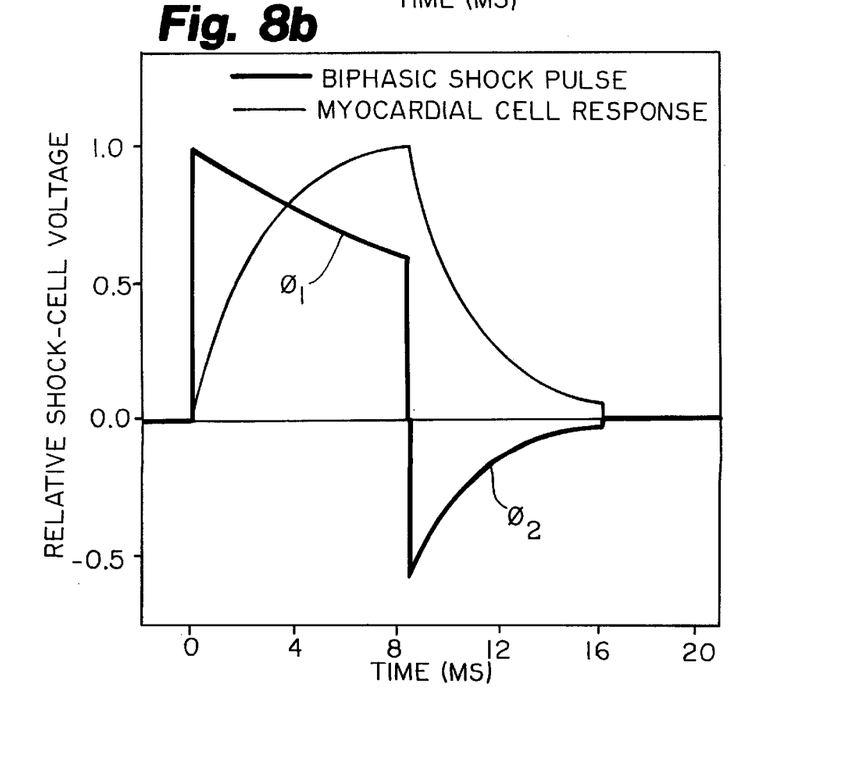
FIG. 8B is a biphasic shock pulse and the associated myocardial cell response generated in accordance with the present invention using Blair-Walcott theory of maximal cell response for the first phase and $2^{nd}$ order charge burping for the second phase.
Figure 8C:
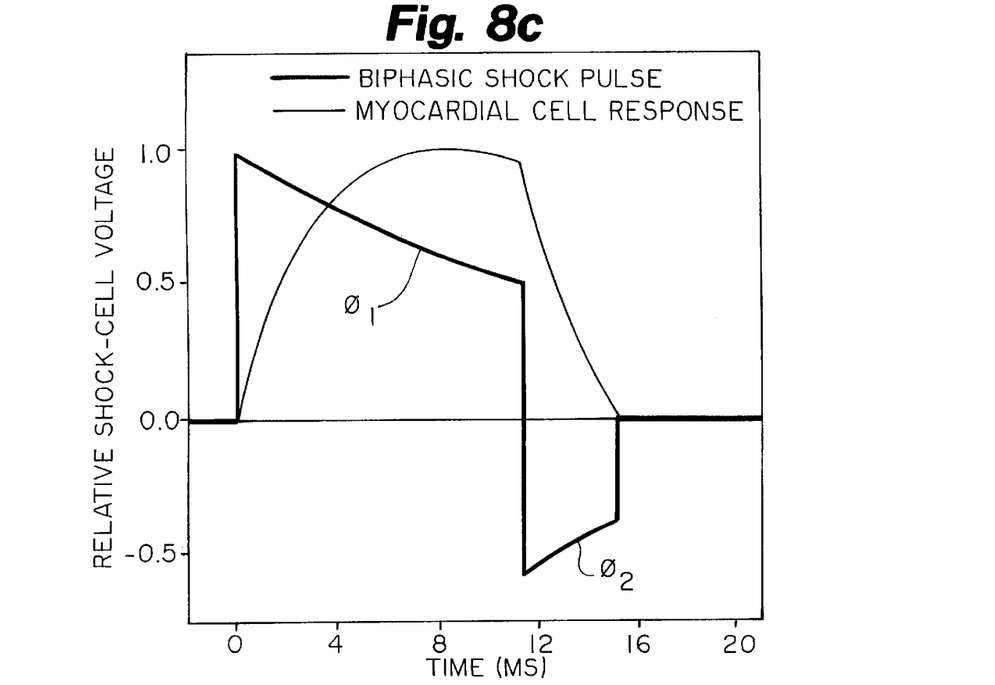
FIG. 8C is a biphasic shock pulse and the associated myocardial cell response generated in accordance with the present invention using Kroll-Irnich theory of effective current for the first phase and $1^{st}$ order charge burping for the second phase.
Figure 8D:
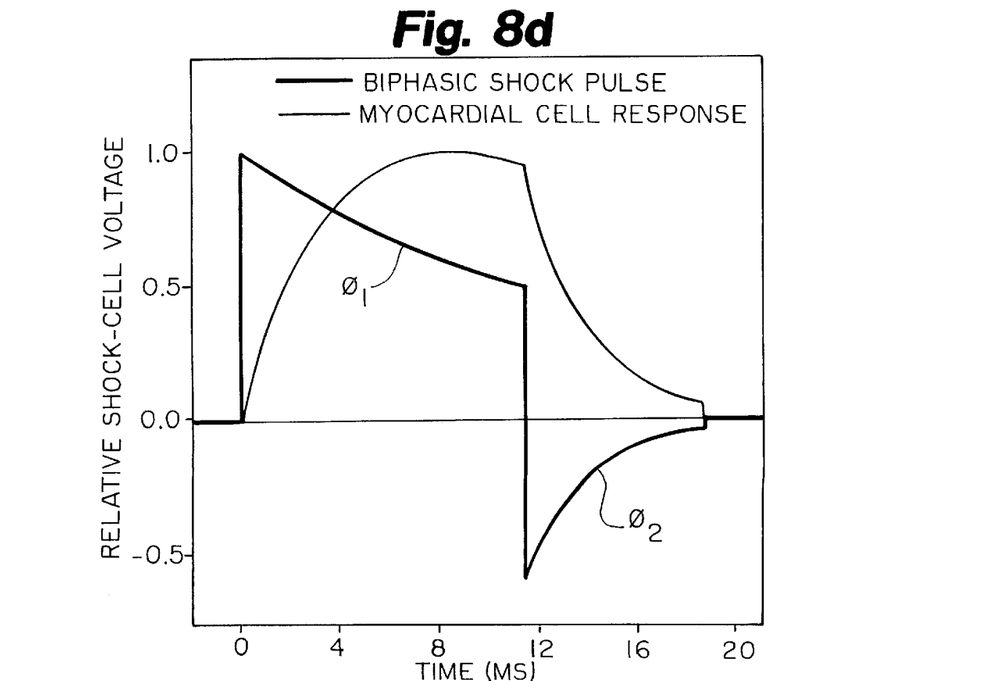
FIG. 8D is a biphasic shock pulse and the associated myocardial cell response generated in accordance with the present invention using Kroll-Irnich theory of effective current for the first phase and $2^{nd}$ order charge burping for the second phase.

The waveform delivery algorithm is phase independent and operates in the same way for each phase of a waveform being discharged. The algorithm uses the tilt expression appropriate for each phase of a waveform. The present invention also generates a waveform to be congruent with the myocardial cell response waveform. Referring now to FIGS. 8A and 8B, first and second order charge burping shock pulses and the corresponding myocardial cell response waveforms may be seen. The waveforms are generated using the Blair-Walcott design model for phase one. In these figures relative shock-cell voltage and time are the design parameters. As can be observed, the biphasic shock pulse simulates the myocardial cell response and there is no interphase duration between $\phi_1$ and $\phi_2$. Similarly, referring now to FIGS. 8C and 8D, first and second order charge burping shock pulses and the myocardial cell response corresponding thereto are shown. The waveforms are generated using the Kroll-Inrich design model for phase one. A monophasic waveform is generated in the same manner as the first phase of the biphasic waveform.

The waveform tilt is adapted to each phase of a waveform. The waveform tilt values are determined from a combination of the Blair-Walcott or Kroll-Inrich theory with first or second order charge burping as previously described in Tables I and II. The waveform tilt data have been fit to analytical expression so that the expression yields a tilt value as a function of resistance. For $\Omega = (V/I)$, the best fit expressions are:

Blair-Walcott $\phi_1$:
  Tilt=122.0–[42.6*Log$_{10}$($\Omega$)];
Kroll-Irnich $\phi_1$:
  Tilt=117.8–[35.4*Log$_{10}$($\Omega$)];
First-order $\phi_2$:
  Tilt=286.6–[206.3*Log$_{10}$($\Omega$)]+[38.6*Log$_{10}$($\Omega$)$^2$];
Second-order $\phi_2$:
  Tilt=–345.8+[527.3*Log$_{10}$($\Omega$)]–[155.5*Log$_{10}$($\Omega$)$^2$].

It should be noted that these analytical expressions depend upon the values chosen for chronaxie and cell membrane time constant. As previously stated, the values chosen for these are merely exemplary values and changes may be made without departing from the spirit or scope of the present invention. These formulas are implemented in the algorithm of the present invention to calculate the waveform tilt of the discharge pulses and shape them accordingly. In the preferred embodiment, the waveforms induce the myocardial profile.

Studies in cardiac tissue stimulation have shown that changing from one phase to another induces propagation from a cathode, and termination (break) from an anode. Thus, in a device such as the external defibrillator of the present invention where a cathode and an anode terminal (electrodes) are used to defibrillate the heart, inducing the second phase $\phi_2$ immediately after the first phase $\phi_1$ provides significant advantages. In other words, the attenuation and preferably the elimination of an interphase duration between phase $\phi_1$ and $\phi_2$ is most desirable. Several studies support the hypothesis that anode and cathode break stimulation occur in cardiac tissue and assist the diffusion of depolarization into a previously hyperpolarized region (See, for example *Mechanisms for Electrical Stimulation of Excitable Tissue*, by Roth B J, *Critical Reviews In Biomedical Engineering* 1994, 22 (3–4) p253–305 ISSN 0278-940X). According to this paper, two mechanisms for defibrillation have been hypothesized: (1) the relatively high junctional resistance between cardiac cells causes each cell to be depolarized on one side and hyperpolarized on the other; and (2) the fiber tracts within the heart behave like individual fibers, with fiber curvature providing a mechanism for polarization. Similarly, other studies confirm simultaneous depolarization and hyperpolarization during stimulation of refractory and excitable tissue that act as virtual anodes and cathodes (See, for example; *Virtual Electrodes in Cardiac Tissue; A Common Mechanism for Anodal and Cathodal Stimulation*; by Wikswo J P Jr.; Lin S F; Abbas R A, *Biophysics Journal* December 1995, 69(6) p32195–210, ISSN 0006-3495). Further, yet another study conducted to numerically simulate electrical stimulation of cardiac tissue was based on four types of excitations which comprise: cathode make (CM), anode make (AM), cathode break (CB) and anode break (AB). The mechanisms of excitation were: for CM, tissue under the cathode was depolarized to threshold; for AM, tissue at a virtual cathode was depolarized to threshold; for CB, a long cathodal pulse produced a steady-state depolarization under the cathode and hyperpolarization at virtual a virtual anode. At the end (break) of the pulse, the depolarization diffused into the hyperpolarized tissue resulting in excitation. For AB, a long anodal pulse produced a steady-state hyperpolarization under the anode and depolarization at a virtual cathode. It was found that at the end (break) of the pulse, the depolarization diffused into the hyperpolarized tissue, resulting in excitation. Strength duration curves for CM and AM were compared. They were found to be similar except when the duration was shorter than 0.2 ms, in which case the AM threshold rose more quickly with decreasing duration than did the CM threshold. Accordingly, it is advantageous to eliminate or at least limit to below 0.2 ms the interphase duration between $\phi_1$ and $\phi_2$ (See, for example, *A Mathematical Model of Make and Break Electrical Stimulation of Cardiac Tissue by a Unipolar Anode or Cathode*; by Roth B J; *IEEE Trans Biomed Eng* December 1995, 42 (12) p1174–84). Yet another study shows interaction between adjacent depolarization and hyperpolarization tissue cause anode-break and cathode-break stimulation (See, for example; *The Effect of Externally Applied Electrical Fields on Myocardial Tissue*; by Roth B J and Wikswo J P Jr.; *Proceedings of the IEEE*, 1996,V84, N3 (MAR), P379–391).

The time-intensity relations of tissue stimulation by electric currents and the associated break phenomenon is well established in the art. In one of the earliest publications, stimulation by breaking constant currents is disclosed. The publication indirectly indicates depolarization and hyperpolarization and the resultant anode-break and cathode-break stimulation (See, for example; *On the Intensity-time Relations for Stimulation by Electric Currents*; by H. A. Blair, *J. Gen. Physiol.* 1932; 15: 731–755).

Accordingly, the advantages of eliminating at best, and/or significantly reducing, the interphase duration between $\phi_1$ and $\phi_2$ is clearly implied in most of the teachings of the references cited in supra. The present invention advantageously utilizes those teachings and provides a continual waveform shape reforming method and device. Specifically, myocardial cell response as well as transchest resistance dynamics are considered to enable the continual waveform shape reforming based on the electrical impedance which varies in the course of a defibrillation pulse delivery.

The invention is not to be taken as limited to all of the details thereof as modifications and variations thereof may be made without departing from the spirit or scope of the invention.

What is claimed is:

1. An external defibrillator device for administering a truncated exponential waveform to a cardiac patient, the device comprising:
   a plurality of external electrodes;
   means for generating a waveform for delivery to the electrodes;
   means for dividing the waveform into discrete time slices during delivery of the waveform, wherein the means for dividing is electrically connected to the means for generating and, wherein the means for dividing includes means for measuring selectable parameters of the waveform at the plurality of external electrodes at one of fixed, variable and increasingly shorter increments of time slices between measurements;
   means for dynamically shaping the waveform electrically connected to the means for generating, wherein the means for dynamically shaping shapes the waveform based on the measured selectable parameters of the waveform;
   means for setting a threshold tilt amount for the tilt of the waveform electrically connected to the means for dynamically shaping; and
   a control circuit for controlling operation of the device electrically connected with the means for generating, the means for dividing, the means for dynamically shaping and the means for setting.

2. The device according to claim 1 including means for setting a threshold tilt amount, the means for setting a threshold tilt amount including means for measuring one of resistance and voltage-current ratio parameters of the waveform to set said threshold tilt amount.

3. The device according to claim 1 wherein said means for dividing said waveform into discrete time slices includes means for measuring voltage and current of the waveform at one of fixed, variable and increasingly longer increments of time slices between measurements.

4. The device according to claim 1 wherein said means for shaping includes means for quantizing parameters of said waveform at said increments of time slices.

5. The device according to claim 4 wherein said means for quantizing further includes means for truncating the waveform at any time without waiting for the waveform to decay to a preset level.

6. The device of claim 1, wherein the waveform comprises a first phase and a second phase.

7. The device of claim 6, wherein said control circuit includes means for transitioning between said first phase and said second phase in a preset time.

8. The device of claim 7, wherein said preset time is less than 0.2 milliseconds.

9. The device of claim 7, wherein said preset time is substantially zero.

10. The device of claim 1, wherein the time slices are approximately 1 millisecond in duration.

11. A method for administering a truncated exponential waveform transchest to a cardiac patient with an external defibrillator comprising the device-implemented steps of:

providing a plurality of external electrodes for positioning on a patient;

setting a threshold tilt amount for the tilt of the waveform;

dividing the waveform into discrete time slices, wherein the time slices have an initial time slice and a series of subsequent time slices;

measuring a discharge voltage and current of the waveform continuously during the delivery of the defibrillation waveform;

calculating a transchest resistance as a function of said discharge voltage and current;

calculating a waveform tilt for said waveform at said initial time slice to determine an initial value of said waveform tilt;

utilizing said waveform tilt to calculate a voltage drop in said discharge voltage;

continuing the delivery of said waveform at said series of subsequent time slices to calculate a corresponding series of waveform tilts and voltages for each of said discrete time slices; and halting the delivery of said waveform when said discharge voltage has dropped by an amount equal to said threshold tilt amount.

12. The method according to claim 11 wherein an algorithm implemented in a programmable processor imposes a step of tilt stopping to continually and dynamically shape said waveform.

13. The method according to claim 12 wherein said step of tilt stopping includes the step of controlling a time delay no greater than 0.2 ms between a first phase ($\phi_1$) and a second phase ($\phi_2$) of a biphasic waveform.

14. The method according to claim 13 wherein said time delay between said $\phi_1$ and said $\phi_2$ is controllable to be substantially near zero.

* * * * *